(12) United States Patent
Swain et al.

(10) Patent No.: US 10,155,074 B2
(45) Date of Patent: Dec. 18, 2018

(54) TISSUE ROLL SCAFFOLDS

(71) Applicant: KCI Licensing, Inc., San Antonio, TX (US)

(72) Inventors: Larry D. Swain, San Antonio, TX (US); Michael E. Manwaring, San Antonio, TX (US); Douglas A. Cornet, Barboursville, VA (US); Braden King-fung Leung, San Antonio, TX (US)

(73) Assignee: KCI Licensing, Inc., San Antonio, TX (US)

( * ) Notice: Subject to any disclaimer, the term of this patent is extended or adjusted under 35 U.S.C. 154(b) by 529 days.

(21) Appl. No.: 14/811,355

(22) Filed: Jul. 28, 2015

(65) Prior Publication Data
US 2015/0328381 A1    Nov. 19, 2015

Related U.S. Application Data

(62) Division of application No. 12/648,475, filed on Dec. 29, 2009, now Pat. No. 9,125,766.
(Continued)

(51) Int. Cl.
*A61M 1/00* (2006.01)
*A61B 17/11* (2006.01)
*A61F 13/00* (2006.01)

(52) U.S. Cl.
CPC ........... *A61M 1/0088* (2013.01); *A61B 17/11* (2013.01); *A61B 17/1128* (2013.01); *A61F 13/00063* (2013.01); *A61F 13/00068* (2013.01)

(58) Field of Classification Search
CPC ............ A61M 1/0088; A61F 13/00068; A61F 13/00063
See application file for complete search history.

(56) References Cited

U.S. PATENT DOCUMENTS 1,355,846 A    10/1920   Rannells
2,547,758 A     4/1951   Kelling
(Continued)

FOREIGN PATENT DOCUMENTS

AU    550575 B2    3/1986
AU    745271 B2    3/2002
(Continued)

OTHER PUBLICATIONS

European Search Report for EP14197314.9, dated Feb. 16, 2015.
(Continued)

*Primary Examiner* — Adam Marcetich
*Assistant Examiner* — Jessica Arble

(57) ABSTRACT

An apparatus and system for treating a wound having a cavity is disclosed. The apparatus has a scaffold including a scaffold lamina and a tissue lamina wherein the scaffold lamina forms a laminate in fluid communication with the tissue lamina. The laminate is rolled into a generally cylindrical shape having two end surfaces. The apparatus further includes a manifold having a port for coupling to a source of reduced pressure and that is positioned in fluid communication with the scaffold to provide reduced pressure to the scaffold lamina and the wound. A method for treating a wound having a cavity is also disclosed and includes positioning a scaffold lamina adjacent a tissue lamina to form a laminate in fluid communication with the tissue lamina, rolling the laminate into a generally cylindrical shape having two end surfaces, and positioning the scaffold within the cavity of the wound.

31 Claims, 6 Drawing Sheets

Related U.S. Application Data

(60) Provisional application No. 61/238,770, filed on Sep. 1, 2009, provisional application No. 61/234,692, filed on Aug. 18, 2009, provisional application No. 61/142,053, filed on Dec. 31, 2008, provisional application No. 61/142,065, filed on Dec. 31, 2008.

(56) References Cited

U.S. PATENT DOCUMENTS

| | | |
|---|---|---|
| 2,632,443 A | 3/1953 | Lesher |
| 2,682,873 A | 7/1954 | Evans et al. |
| 2,910,763 A | 11/1959 | Lauterbach |
| 2,969,057 A | 1/1961 | Simmons |
| 3,066,672 A | 12/1962 | Crosby, Jr. et al. |
| 3,367,332 A | 2/1968 | Groves |
| 3,520,300 A | 7/1970 | Flower, Jr. |
| 3,568,675 A | 3/1971 | Harvey |
| 3,648,692 A | 3/1972 | Wheeler |
| 3,682,180 A | 8/1972 | McFarlane |
| 3,826,254 A | 7/1974 | Mellor |
| 4,080,970 A | 3/1978 | Miller |
| 4,096,853 A | 6/1978 | Weigand |
| 4,139,004 A | 2/1979 | Gonzalez, Jr. |
| 4,165,748 A | 8/1979 | Johnson |
| 4,184,510 A | 1/1980 | Murry et al. |
| 4,233,969 A | 11/1980 | Lock et al. |
| 4,245,630 A | 1/1981 | Lloyd et al. |
| 4,256,109 A | 3/1981 | Nichols |
| 4,261,363 A | 4/1981 | Russo |
| 4,275,721 A | 6/1981 | Olson |
| 4,284,079 A | 8/1981 | Adair |
| 4,297,995 A | 11/1981 | Golub |
| 4,333,468 A | 6/1982 | Geist |
| 4,373,519 A | 2/1983 | Errede et al. |
| 4,382,441 A | 5/1983 | Svedman |
| 4,392,853 A | 7/1983 | Muto |
| 4,392,858 A | 7/1983 | George et al. |
| 4,419,097 A | 12/1983 | Rowland |
| 4,465,485 A | 8/1984 | Kashmer et al. |
| 4,475,909 A | 10/1984 | Eisenberg |
| 4,480,638 A | 11/1984 | Schmid |
| 4,525,166 A | 6/1985 | Leclerc |
| 4,525,374 A | 6/1985 | Vaillancourt |
| 4,540,412 A | 9/1985 | Van Overloop |
| 4,543,100 A | 9/1985 | Brodsky |
| 4,548,202 A | 10/1985 | Duncan |
| 4,551,139 A | 11/1985 | Plaas et al. |
| 4,569,348 A | 2/1986 | Hasslinger |
| 4,605,399 A | 8/1986 | Weston et al. |
| 4,608,041 A | 8/1986 | Nielsen |
| 4,640,688 A | 2/1987 | Hauser |
| 4,655,754 A | 4/1987 | Richmond et al. |
| 4,664,662 A | 5/1987 | Webster |
| 4,710,165 A | 12/1987 | McNeil et al. |
| 4,733,659 A | 3/1988 | Edenbaum et al. |
| 4,743,232 A | 5/1988 | Kruger |
| 4,758,220 A | 7/1988 | Sundblom et al. |
| 4,787,888 A | 11/1988 | Fox |
| 4,787,906 A | 11/1988 | Haris |
| 4,826,494 A | 5/1989 | Richmond et al. |
| 4,838,883 A | 6/1989 | Matsuura |
| 4,840,187 A | 6/1989 | Brazier |
| 4,863,449 A | 9/1989 | Therriault et al. |
| 4,872,450 A | 10/1989 | Austad |
| 4,878,901 A | 11/1989 | Sachse |
| 4,897,081 A | 1/1990 | Poirier et al. |
| 4,906,233 A | 3/1990 | Moriuchi et al. |
| 4,906,240 A | 3/1990 | Reed et al. |
| 4,919,654 A | 4/1990 | Kalt |
| 4,941,882 A | 7/1990 | Ward et al. |
| 4,953,565 A | 9/1990 | Tachibana et al. |
| 4,969,880 A | 11/1990 | Zamierowski |
| 4,985,019 A | 1/1991 | Michelson |
| 5,037,397 A | 8/1991 | Kalt et al. |
| 5,086,170 A | 2/1992 | Luheshi et al. |
| 5,092,858 A | 3/1992 | Benson et al. |
| 5,100,396 A | 3/1992 | Zamierowski |
| 5,134,994 A | 8/1992 | Say |
| 5,149,331 A | 9/1992 | Ferdman et al. |
| 5,167,613 A | 12/1992 | Karami et al. |
| 5,176,663 A | 1/1993 | Svedman et al. |
| 5,215,522 A | 6/1993 | Page et al. |
| 5,232,453 A | 8/1993 | Plass et al. |
| 5,261,893 A | 11/1993 | Zamierowski |
| 5,278,100 A | 1/1994 | Doan et al. |
| 5,279,550 A | 1/1994 | Habib et al. |
| 5,298,015 A | 3/1994 | Komatsuzaki et al. |
| 5,342,376 A | 8/1994 | Ruff |
| 5,344,415 A | 9/1994 | DeBusk et al. |
| 5,358,494 A | 10/1994 | Svedman |
| 5,437,622 A | 8/1995 | Carion |
| 5,437,651 A | 8/1995 | Todd et al. |
| 5,527,293 A | 6/1996 | Zamierowski |
| 5,549,584 A | 8/1996 | Gross |
| 5,556,375 A | 9/1996 | Ewall |
| 5,607,388 A | 3/1997 | Ewall |
| 5,636,643 A | 6/1997 | Argenta et al. |
| 5,645,081 A | 7/1997 | Argenta et al. |
| 6,071,267 A | 6/2000 | Zamierowski |
| 6,103,255 A | 8/2000 | Levene et al. |
| 6,135,116 A | 10/2000 | Vogel et al. |
| 6,241,747 B1 | 6/2001 | Ruff |
| 6,287,316 B1 | 9/2001 | Agarwal et al. |
| 6,345,623 B1 | 2/2002 | Heaton et al. |
| 6,365,146 B1 | 4/2002 | Uhrich |
| 6,488,643 B1 | 12/2002 | Tumey et al. |
| 6,493,568 B1 | 12/2002 | Bell et al. |
| 6,553,998 B2 | 4/2003 | Heaton et al. |
| 6,695,823 B1 | 2/2004 | Lina et al. |
| 6,696,575 B2 | 2/2004 | Schmidt et al. |
| 6,767,334 B1 | 7/2004 | Randolph |
| 6,814,079 B2 | 11/2004 | Heaton et al. |
| 6,856,821 B2 | 2/2005 | Johnson |
| 6,936,037 B2 | 8/2005 | Bubb et al. |
| 6,951,553 B2 | 10/2005 | Bubb et al. |
| 6,994,702 B1 | 2/2006 | Johnson |
| 7,004,915 B2 | 2/2006 | Boynton et al. |
| 7,070,584 B2 | 7/2006 | Johnson et al. |
| 7,077,832 B2 | 7/2006 | Fleischmann |
| 7,108,683 B2 | 9/2006 | Zamierowski |
| 7,160,553 B2 | 1/2007 | Gibbins et al. |
| 7,214,202 B1 | 5/2007 | Vogel et al. |
| 7,279,612 B1 | 10/2007 | Heaton et al. |
| 7,316,672 B1 | 1/2008 | Hunt et al. |
| 7,346,945 B2 | 3/2008 | Phillips et al. |
| 7,351,250 B2 | 4/2008 | Zamierowski |
| 7,384,786 B2 | 6/2008 | Freyman et al. |
| 7,465,298 B2 | 12/2008 | Seward et al. |
| 2002/0077661 A1 | 6/2002 | Saadat |
| 2002/0115951 A1 | 8/2002 | Norstrem et al. |
| 2002/0120185 A1 | 8/2002 | Johnson |
| 2002/0143286 A1 | 10/2002 | Tumey |
| 2003/0225347 A1 | 12/2003 | Argenta et al. |
| 2005/0260189 A1 | 11/2005 | Klibanov et al. |
| 2006/0041247 A1* | 2/2006 | Petrosenko ............ A61F 13/00 604/543 |
| 2006/0084930 A1* | 4/2006 | Dhanaraj ................ A61L 15/26 604/305 |
| 2007/0123895 A1 | 5/2007 | Lytinas |
| 2007/0218101 A1* | 9/2007 | Johnson ................ A61B 17/88 424/423 |
| 2008/0033324 A1 | 2/2008 | Cornet et al. |
| 2008/0208358 A1 | 8/2008 | Bellamkonda et al. |

FOREIGN PATENT DOCUMENTS

| | | |
|---|---|---|
| AU | 755496 B2 | 12/2002 |
| CA | 2005436 A1 | 6/1990 |
| DE | 26 40 413 A1 | 3/1978 |
| DE | 43 06 478 A1 | 9/1994 |
| DE | 29 504 378 U1 | 9/1995 |
| EP | 0100148 A1 | 2/1984 |
| EP | 0117632 A2 | 9/1984 |
| EP | 0161865 A2 | 11/1985 |

(56) References Cited

FOREIGN PATENT DOCUMENTS

| | | | |
|---|---|---|---|
| EP | 0358302 A2 | 3/1990 | |
| EP | 1018967 A1 | 7/2000 | |
| EP | 1923019 A1 | 5/2008 | |
| GB | 692578 A | 6/1953 | |
| GB | 2 195 255 A | 4/1988 | |
| GB | 2 197 789 A | 6/1988 | |
| GB | 2 220 357 A | 1/1990 | |
| GB | 2 235 877 A | 3/1991 | |
| GB | 2 329 127 A | 3/1999 | |
| GB | 2 333 965 A | 8/1999 | |
| JP | 4129536 B2 | 8/2008 | |
| SG | 71559 | 4/2002 | |
| WO | 80/02182 A1 | 10/1980 | |
| WO | 87/04626 A1 | 8/1987 | |
| WO | 90/010424 A1 | 9/1990 | |
| WO | 93/009727 A1 | 5/1993 | |
| WO | 94/020041 A1 | 9/1994 | |
| WO | WO 9420152 A1 * | 9/1994 | .......... A61M 1/0084 |
| WO | 96/05873 A1 | 2/1996 | |
| WO | 97/18007 A1 | 5/1997 | |
| WO | 0038755 A2 | 7/2000 | |
| WO | 0061206 A1 | 10/2000 | |
| WO | 03-018098 A2 | 11/2003 | |
| WO | 03/092620 A2 | 11/2003 | |
| WO | 04/060148 A2 | 7/2004 | |
| WO | 04/105576 A2 | 12/2004 | |
| WO | 05/009488 A2 | 2/2005 | |
| WO | 05/033273 A2 | 4/2005 | |
| WO | 06/004951 A2 | 1/2006 | |
| WO | 06/127853 A2 | 11/2006 | |
| WO | 2007015964 A1 | 2/2007 | |
| WO | 07/067685 A2 | 6/2007 | |
| WO | 07092397 A2 | 8/2007 | |
| WO | 07/106589 A2 | 9/2007 | |
| WO | 07/106591 A2 | 9/2007 | |
| WO | 2007/106590 A2 | 9/2007 | |
| WO | 2007/106592 A2 | 9/2007 | |
| WO | 2007/106594 A2 | 9/2007 | |
| WO | 07/133555 A2 | 11/2007 | |
| WO | 07/133556 A2 | 11/2007 | |
| WO | 07/143060 A2 | 12/2007 | |
| WO | 2008013896 A2 | 1/2008 | |
| WO | 08/036162 A2 | 3/2008 | |
| WO | 08/036359 A2 | 3/2008 | |
| WO | 08/036361 A2 | 3/2008 | |
| WO | 08/042481 A2 | 4/2008 | |
| WO | 2008091521 A2 | 7/2008 | |

OTHER PUBLICATIONS

Louis C. Argenta, MD and Michael J. Morykwas, PHD; Vacuum-Assisted Closure: A New Method for Wound Control and Treatment: Clinical Experience; Annals of Plastic Surgery.
Susan Mendez-Eatmen, RN; "When wounds Won't Heal" RN Jan. 1998, vol. 61 (1); Medical Economics Company, Inc., Montvale, NJ, USA; pp. 20-24.
James H. Blackburn II, MD et al.: Negative-Pressure Dressings as a Bolster for Skin Grafts; Annals of Plastic Surgery, vol. 40, No. 5, May 1998, pp. 453-457; Lippincott Williams & Wilkins, Inc., Philidelphia, PA, USA.
John Masters; "Reliable, Inexpensive and Simple Suction Dressings"; Letter to the Editor, British Journal of Plastic Surgery, 198, vol. 51 (3), p. 267; Elsevier Science/The British Association of Plastic Surgeons, UK.
S.E. Greer, et al. "The Use of Subatmospheric Pressure Dressing Therapy to Close Lymphocutaneous Fistulas of the Groin" British Journal of Plastic Surgery (2000), 53, pp. 484-487.
George V. Letsou, MD., et al; "Stimulation of Adenylate Cyclase Activity in Cultured Endothelial Cells Subjected to Cyclic Stretch"; Journal of Cardiovascular Surgery, 31, 1990, pp. 634-639.
Orringer, Jay, et al; "Management of Wounds in Patients with Complex Enterocutaneous Fistulas"; Surgery, Gynecology & Obstetrics, Jul. 1987, vol. 165, pp. 79-80.
International Search Report for PCT International Application PCT/GB95/01983; dated Nov. 23, 1995.
PCT International Search Report for PCT International Application PCT/GB98/02713; dated Jan. 8, 1999.
PCT Written Opinion; PCT International Application PCT/GB98/02713; dated Jun. 8, 1999.
PCT International Examination and Search Report, PCT International Application PCT/GB96/02802; dated Jan. 15, 1998 & Apr. 29, 1997.
PCT Written Opinion, PCT International Application PCT/GB96/02802; dated Sep. 3, 1997.
Dattilo, Philip P., Jr., et al; "Medical Textiles: Application of an Absorbable Barbed Bi-directional Surgical Suture"; Journal of Textile and Apparel, Technology and Management, vol. 2, Issue 2, Spring 2002, pp. 1-5.
Kostyuchenok, B.M., et al; "Vacuum Treatment in the Surgical Management of Purulent Wounds"; Vestnik Khirurgi, Sep. 1986, pp. 18-21 and 6 page English translation thereof.
Davydov, Yu. A., et al; "Vacuum Therapy in the Treatment of Purulent Lactation Mastitis"; Vestnik Khirurgi, May 14, 1986, pp. 66-70, and 9 page English translation thereof.
Yusupov. Yu.N., et al; "Active Wound Drainage", Vestnki Khirurgi, vol. 138, Issue 4, 1987, and 7 page English translation thereof.
Davydov, Yu.A., et al; "Bacteriological and Cytological Assessment of Vacuum Therapy for Purulent Wounds"; Vestnik Khirugi, Oct. 1988, pp. 48-52, and 8 page English translation thereof.
Davydov, Yu.A., et al; "Concepts for the Clinical-Biological Management of the Wound Process in the Treatment of Purulent Wounds by Means of Vacuum Therapy"; Vestnik Khirurgi, Jul. 7, 1980, pp. 132-136, and 8 page English translation thereof.
Chariker, Mark E., M.D., et al; "Effective Management of incisional and cutaneous fistulae with closed suction wound drainage"; Contemporary Surgery, vol. 34, Jun. 1989, pp. 59-63.
Egnell Minor, Instruction Book, First Edition, 300 7502, Feb. 1975, pp. 24.
Egnell Minor: Addition to the Users Manual Concerning Overflow Protection—Concerns all Egnell Pumps, Feb. 3, 1983, pp. 2.
Chinn, Steven D. et al.: "Closed Wound Suction Drainage", The Journal of Foot Surgery, vol. 24, No. 1, 1985, pp. 76-81.
Arnljots, Björn et al.: "Irrigation Treatment in Split-Thickness Skin Grafting of Intractable Leg Ulcers", Scand J. Plast Reconstr. Surg., No. 19, 1985, pp. 211-213.
Svedman, P.: "A Dressing Allowing Continuous Treatment of a Biosurface", IRCS Medical Science: Biomedical Technology, Clinical Medicine, Surgery and Transplantation, vol. 7, 1979, p. 221.
Svedman, P. et al: "A Dressing System Providing Fluid Supply and Suction Drainage Used for Continuous of Intermittent Irrigation", Annals of Plastic Surgery, vol. 17, No. 2, Aug. 1986, pp. 125-133.
N.A. Bagautdinov, "Variant of External Vacuum Aspiration in the Treatment of Purulent Diseases of Soft Tissues," Current Problems in Modern Clinical Surgery: Interdepartmental Collection, edited by V. Ye Volkov et al. (Chuvashia State University, Cheboksary, U.S.S.R. 1986); pp. 94-96 (copy and certified translation).
K.F. Jeter, T.E. Tintle, and M. Chariker, "Managing Draining Wounds and Fistulae: New and Established Methods," Chronic Wound Care, edited by D. Krasner (Health Management Publications, Inc., King of Prussia, PA 1990), pp. 240-246.
G. Živadinovi?, V. ?uki?, Ž. Maksimovi?, ?. Radak, and P. Peška, "Vacuum Therapy in the Treatment of Peripheral Blood Vessels," Timok Medical Journal 11 (1986), pp. 161-164 (copy and certified translation).
F.E. E Johnson, "An Improved Technique for Skin Graft Placement Using a Suction Drain," Surgery, Gynecology, and Obstetrics 159 (1984), pp. 584-585.
A.A. Safronov, Dissertation Abstract, Vacuum Therapy of Trophic Ulcers of the Lower Leg with Simultaneous Autoplasty of the Skin (Central Scientific Research Institute of Traumatology and Orthopedics, Moscow, U.S.S.R. 1967) (copy and certified translation).
M. Schein, R. Saadia, J.R. Jamieson, and G.A.G. Decker, "The 'Sandwich Technique' in the Management of the Open Abdomen," British Journal of Surgery 73 (1986), pp. 369-370.
D.E. Tribble, An Improved Sump Drain-Irrigation Device of Simple Construction, Archives of Surgery 105 (1972) pp. 511-513.

(56) References Cited

OTHER PUBLICATIONS

M.J. Morykwas, L.C. Argenta, E.I. Shelton-Brown, and W. McGuirt, "Vacuum-Assisted Closure: A New Method for Wound Control and Treatment: Animal Studies and Basic Foundation," Annals of Plastic Surgery 38 (1997), pp. 553-562 (Morykwas I).

Selections from W. Meyer and V. Schmieden, Bier's Hyperemic Treatment in Surgery, Medicine, and the Specialties: A Manual of Its Practical Application, (W.B. Saunders Co., Philadelphia, PA 1909), pp. 17-25, 44-64, 90-96, 167-170, and 210-211.

V.A. Kuznetsov & N.a. Bagautdinov, "Vacuum and Vacuum-Sorption Treatment of Open Septic Wounds," in II All-Union Conference on Wounds and Wound Infections: Presentation Abstracts, edited by B.M. Kostyuchenok et al. (Moscow, U.S.S.R. Oct. 28-29, 1986) pp. 91-92 ("Bagautdinov II").

V.A. Solovev, Dissertation Abstract, Treatment and Prevention of Suture Failures after Gastric Resection (S.M. Kirov Gorky State Medical Institute, Gorky, U.S.S.R. 1988) ("Solovev Abstract").

V.A.C.® Therapy Clinical Guidelines: A Reference Source for Clinicians; Jul. 2007.

Anderson et al., "Design of Tissue Engineering Scaffolds as Delivery Devices for Mechanical and Mechanically Modulated Signals" Tissue Eng. 13:2525-38 (2007).

Brody et al., "Approaches to Heart Valve Tissue Engineering Scaffold Design" Biomed Mater Res B Appl Biomater. 83:16-43 (2007).

Gemmiti et al., "Fluid Flow Increases Type II Collagen Deposition and Tensile Mechanical Properties in Bioreactor-Grown Tissue-Engineered Cartilage", Tissue Eng. 12:469-79 (2006).

Lago et al., "Neurobiological Assessment of Regenerative Electrodes for Bidirectional Interfacing Injured Peripheral Nerves," IEEE Trans. Biomed. Eng. 54: 1129-37 (2007).

Ma PX and Elisseeff J. ed. Scaffolding in Tissue Engineering, CRC, ISBN 1574445219 (2005) pp. 13-25, 189-197 and 585-608.

Manwaring et al., Characterization of Rat Meningeal Cultures on Materials of Differing Surface Chemistry, Biomaterials 22:3155-3168 (2001).

Manwaring et al., "Contact Guidance Induced Organization of Extracellular Matrix," Biomaterials 25: 3631-3638 (2004).

Mercier et al., "Poly(lactide-co-glycolide) Microspheres as a Moldable Scaffold for Cartilage Tissue Engineering," Biomaterials 26:1945-1952 (2005).

Mikos et al., "Preparation of Poly(glycolic acid) Bonded Fiber Structures for Cell Attachment and Transplantation," J. Biomed. Mater. Res 27: 183-189 (2004).

Norman et al., "Methods for Fabrication of Nanoscale Topography for Tissue Engineering Scaffolds," Ann Biomed Eng 34: 89-101(2006).

Pfister et al., "Neural Engineering to Produce in Vitro Nerve Constructs and Neurointerface," Neurosurgery 60: 137-41 (2007).

Saltzman WM, Tissue Engineering: Engineering Principles for the Design of Replacement Organs and Tissues, Oxford ISBN 019514130X (2004); pp. 318-347; 348-385 and 453-484.

Sachlos et al., "Making Tissue Engineering Scaffolds Work. Review on the Application of Solid Feeform Fabrication Technology to the Production of Tissue Engineering Scaffolds," Eur. Cells and Mat 5:29-40 (2003).

Segvich et al., "Uniform Deposition fo Protein Incorporated Mineral Layer on Three-Dimensional Porous Polymer Scaffolds," J. Biomed Mater Res B: Appl. Biomater 84B: 340-349 (2008).

Shimko et al., "Effect of Porosity on the Fluid Flow Characteristics and Mechanical Properties of Tantalum Scaffolds," J. Biomed Mater Res B: Appl Biomater 73:315-24 (2005).

Takahashi et al., "Induction of Pluripotent Stem Cells from Mouse Embryonic and Adult Fibroblast Cultures by Defined Factores," Cell 126:663-76 (2006).

Tan et al., "Osteocytes Subjected to Fluid Flow Inhibit Osteoclast Formation and Bone Resorption," Bone 41:745-751 (2007).

Tan et al., "Inhibition of Osteocyte Apoptosis by Fluid Flow is Mediated by Nitric Oxide," Biochem Biophys Res Comm 369: 1150-1154 (2008).

Walsh et al., "Directional Neurite Outgrowth is Enhanced by Engineered Meningeal Cell-Coated Substrates," Tissue Eng. 11:1085-1094 (2005).

Wen X et al., pp. 1-23 in Handbook of Nanostructured Biomaterials and Their Applications in Nanobiotechnology, H.S. Nalwa, ed. ISBN 1-58883-033-0 (2005); pp. 393-414.

\* cited by examiner

TISSUE ROLL SCAFFOLDS

CROSS-REFERENCE TO RELATED APPLICATIONS

This application is a Divisional of U.S. patent application Ser. No. 12/648,475, filed on Dec. 29, 2009 which claims priority to U.S. Provisional Application Nos. 61/142,053 and 61/142,065, each filed on Dec. 31, 2008. This application also claims priority to U.S. Provisional Application No. 61/234,692, filed on Aug. 18, 2009 and U.S. Provisional Application No. 61/238,770, filed on Sep. 1, 2009. Each of the foregoing applications is incorporated herein by reference in their entirety.

BACKGROUND

1. Field of the Invention

The present application relates generally to tissue engineering and in particular to apparatuses and systems suitable for use as scaffolds in the treatment of wounds.

2. Description of Related Art

Clinical studies and practice have shown that providing a reduced pressure in proximity to a tissue site augments and accelerates the growth of new tissue at the tissue site. The applications of this phenomenon are numerous, but application of reduced pressure has been particularly successful in treating wounds. This treatment (frequently referred to in the medical community as "negative pressure wound therapy," "reduced pressure therapy," or "vacuum therapy") provides a number of benefits, including faster healing and increased formation of granulation tissue. Typically, reduced pressure has been applied to tissue through a porous pad or other manifolding device. The porous pad contains pores that are capable of distributing reduced pressure to the tissue and channeling fluids that are drawn from the tissue. The porous pad often is incorporated into a dressing having other components that facilitate treatment. A scaffold can also be placed into a defect to support tissue growth into the defect. The scaffold is usually bioabsorbable, leaving new tissue in its place.

Scaffolds for reduced pressure treatment are described in, e.g., WO08/091521, WO07/092397, WO07/106594. The adequacy of current scaffolds can be evaluated in light of knowledge of wound healing. Injury to body tissues results in a wound healing response with sequential stages of healing that include hemostasis (seconds to hours), inflammation (hours to days), repair (days to weeks), and remodeling (weeks to months). A high level of homology exists across most tissue types with regards to the early phases of the wound healing process. However, the stages of healing for various tissues begin to diverge as time passes, with involvement of different types of growth factors, cytokines, and cells. The later stages of the wound healing response are dependent upon the previous stages, with increasing complexity in the temporal patterning of and interrelationships between each component of the response.

Strategies to facilitate normal repair, regeneration, and restoration of function for damaged tissues have focused on methods to support and augment particular steps within this healing response, especially the latter aspects of it. To this end, growth factors, cytokines, extracellular matrix (ECM) analogs, exogenous cells and various scaffolding technologies have been applied alone or in combination with one another. Although some level of success has been achieved using this approach, several key challenges remain. One main challenge is that the timing and coordinated influence of each cytokine and growth factor within the wound healing response complicate the ability to add individual exogenous factors at the proper time and in the correct coordination pattern. The introduction of exogenous cells also faces additional complications due to their potential immunogenicity as well as difficulties in maintaining cell viability.

Synthetic and biologic scaffolds have been utilized to provide three-dimensional frameworks for augmenting endogenous cell attachment, migration, and colonization. To date nearly all scaffolds have been designed with the idea that they can be made to work with the biology. Traditional scaffolding technologies, however, rely on the passive influx of endogenous proteins, cytokines, growth factors, and cells into the interstitium of the porous scaffold. As such, the colonization of endogenous cells into the scaffold is limited by the distance away from vascular elements, which provide nutrient support within a diffusion limit of the scaffold, regardless of tissue type. In addition, the scaffolds can also elicit an immunogenic or foreign body response that leads to an elongated repair process and formation of a fibrous capsule around the implant. Taken together, these complications can all lead to less than functional tissue regeneration at the implantation or injury site.

It would therefore be advantageous to provide additional systems for the repair and remodeling of specialized tissues. The present invention provides such systems.

SUMMARY

The systems, apparatuses, and methods of the illustrative embodiments described herein provide active guidance of tissue repair and regeneration through an implanted scaffold and manifold. In one embodiment, an apparatus for treating a wound having a cavity is disclosed. The apparatus comprises a scaffold including a scaffold lamina and a tissue lamina wherein the scaffold lamina has edges and forms a laminate in fluid communication with the tissue lamina. The laminate is rolled into a generally cylindrical shape having two end surfaces. The rolled scaffold is positioned within the cavity of the wound and provides reduced pressure to the wound. The apparatus further comprises a manifold having a port for coupling to a source of reduced pressure that is positioned in fluid communication with the scaffold to provide reduced pressure to the scaffold lamina and the wound. The apparatus may also comprise a drape formed of substantially impermeable material to cover the scaffold and the manifold within the wound to substantially maintain the reduced pressure within the wound when provided by the manifold. Reduced pressure may likewise be maintained within the wound by closure of the soft tissues and skin over the wound or application site.

In another embodiment, a method for treating a wound having a cavity is also disclosed and comprises positioning a scaffold lamina adjacent a tissue lamina to form a laminate in fluid communication with the tissue lamina, rolling the laminate into a generally cylindrical shape having two end surfaces, and positioning the scaffold within the cavity of the wound to provide reduced pressure to the wound. The method further comprises positioning a manifold in fluid communication with the scaffold to provide reduced pressure to the scaffold lamina and the wound, and then covering the scaffold and the manifold within the wound with a substantially impermeable material to maintain the reduced pressure within the wound when provided by the manifold. Reduced pressure may likewise be maintained within the wound by closure of the soft tissues and skin over the wound or application site.

DETAILED DESCRIPTION

In the following detailed description of the illustrative embodiments, reference is made to the accompanying drawings that form a part hereof. These embodiments are described in sufficient detail to enable those skilled in the art to practice the invention, and it is understood that other embodiments may be utilized and that logical structural, mechanical, electrical, and chemical changes may be made without departing from the spirit or scope of the invention. To avoid detail not necessary to enable those skilled in the art to practice the embodiments described herein, the description may omit certain information known to those skilled in the art. The following detailed description is, therefore, not to be taken in a limiting sense, and the scope of the illustrative embodiments are defined only by the appended claims.

The term "reduced pressure" as used herein generally refers to a pressure less than the ambient pressure at a tissue site that is being subjected to treatment. In most cases, this reduced pressure will be less than the atmospheric pressure at which the patient is located. Alternatively, the reduced pressure may be less than a hydrostatic pressure associated with tissue at the tissue site. Although the terms "vacuum" and "negative pressure" may be used to describe the pressure applied to the tissue site, the actual pressure applied to the tissue site may be significantly more than the pressure normally associated with a complete vacuum. Reduced pressure may initially generate fluid flow in the area of the tissue site. As the hydrostatic pressure around the tissue site approaches the desired reduced pressure, the flow may subside, and the reduced pressure is then maintained. Unless otherwise indicated, values of pressure stated herein are gauge pressures. Similarly, references to increases in reduced pressure typically refer to a decrease in absolute pressure, while decreases in reduced pressure typically refer to an increase in absolute pressure.

Figure 1A:
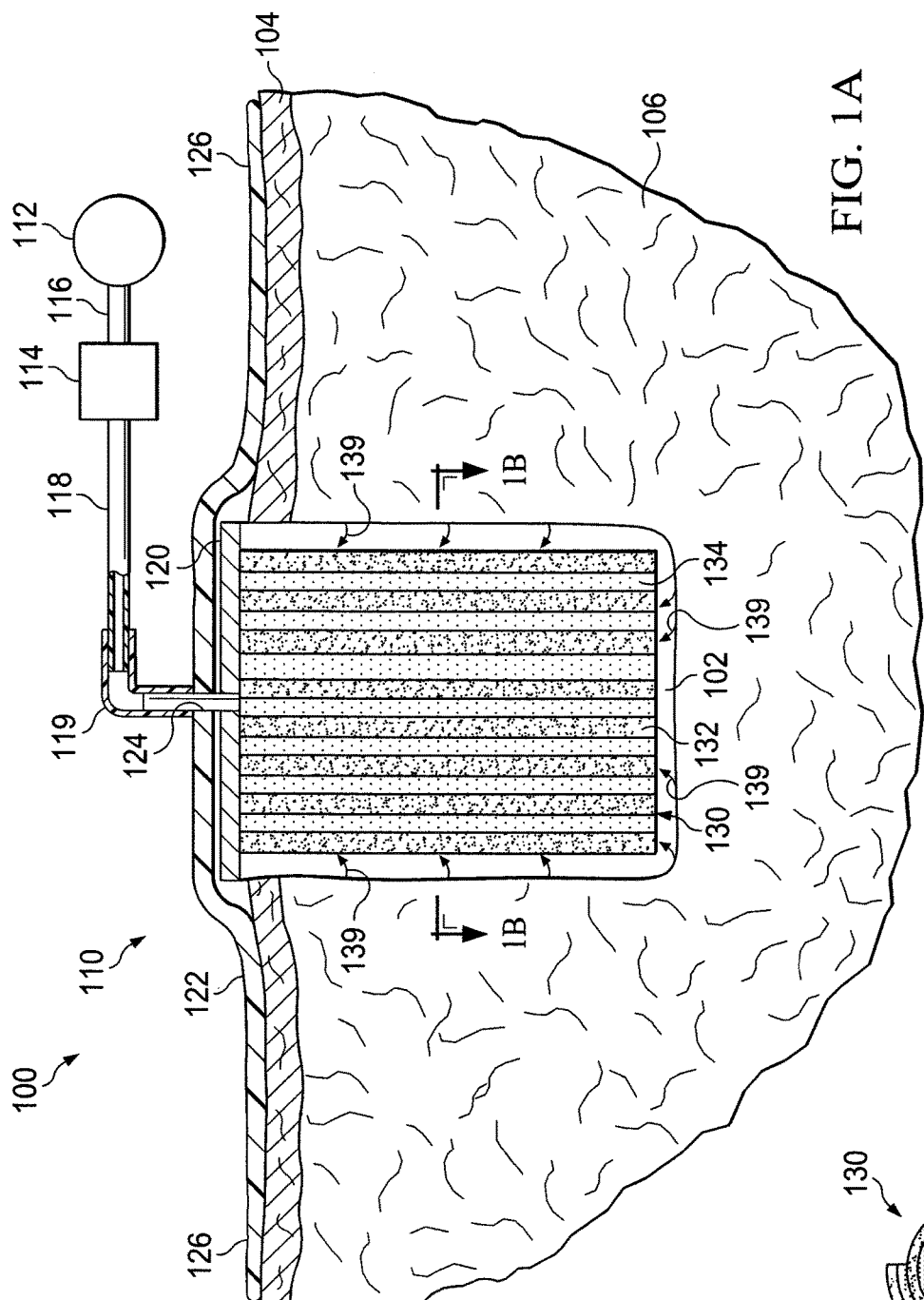
FIG. 1A is a schematic cross-section of a first illustrative embodiment of a system for treating a surface wound on a patient including a composite scaffold and a side-mounted manifold.
Figure 1B:
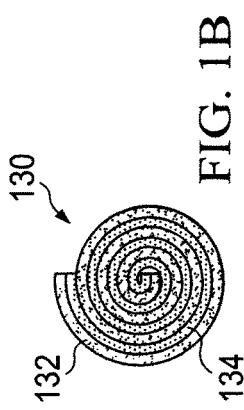
FIG. 1B is a cross-section of the composite scaffold taken on the line 1B-1B in FIG. 1A.
Figure 2:
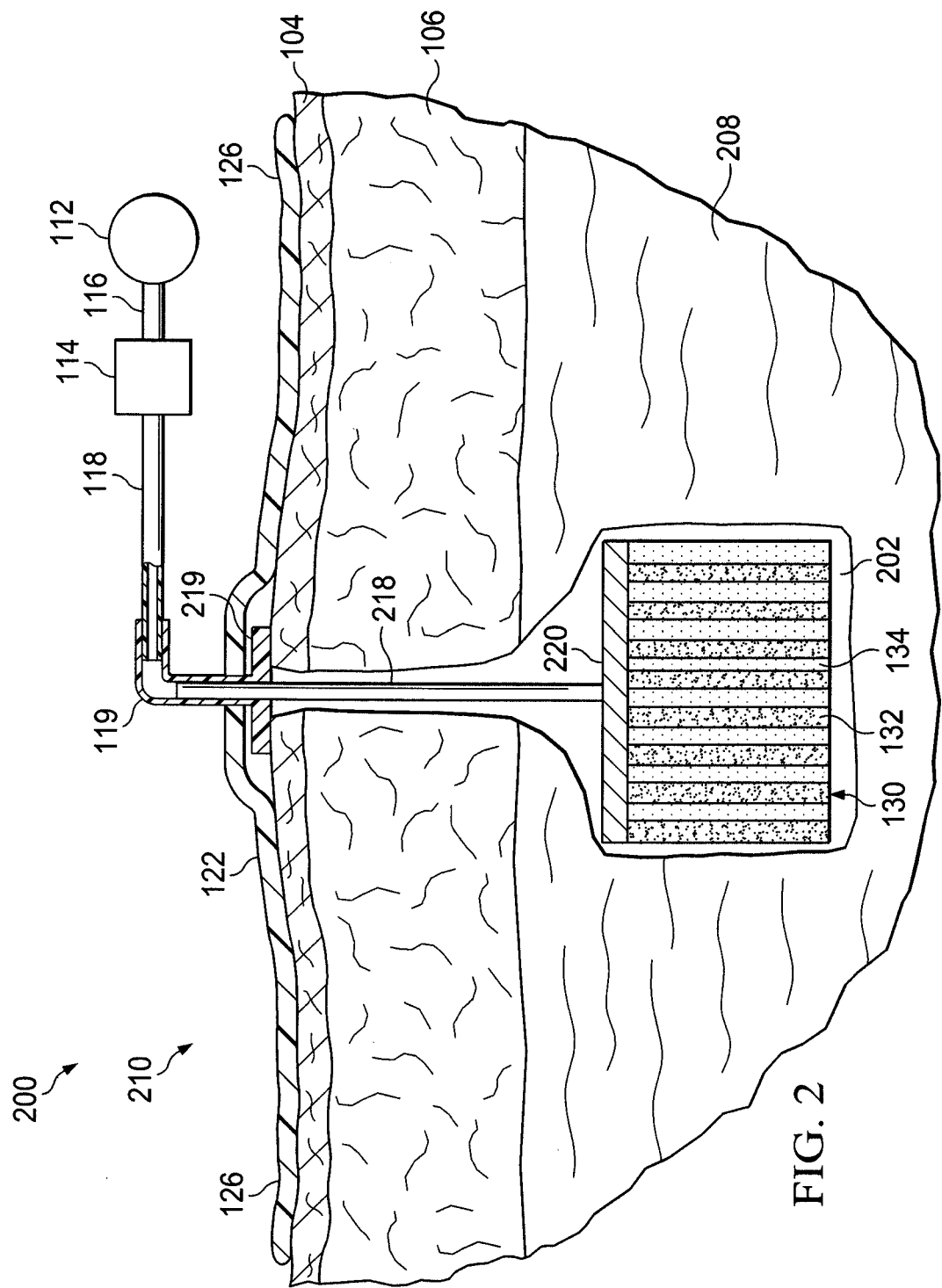
FIG. 2 is a schematic cross-section of a second illustrative embodiment of a system for treating a subcutaneous wound on a patient including a composite scaffold and a side-mounted manifold.

Referring to FIGS. 1A and 1B, a first illustrative embodiment of a reduced-pressure system 100 for applying reduced pressure at a tissue site in the body of a patient to repair a defect. As used herein the term "defect" refers to a tissue site in need of tissue repair or bulking. For example, the defect may be a wound such as a laceration, an incision, a burn or an ulcer. A defect may also be an induced defect such as an incision or puncture made by a surgeon in otherwise healthy tissue for the purposes of bulking the tissue (e.g., such as in cosmetic surgery). Examples of tissue sites that may be bulked by implantation of an apparatus according to the invention include, but are not limited to, the breasts, buttocks, neck and face (e.g., the lips, chin or cheeks). For example, FIG. 1A shows a surface wound 102 having an opening in the epidermis 104 extending into the dermis 106 and forming a cavity. The surface wound may extend to different depths including into the subcutaneous tissue (not shown) below the dermis 106. Referring to FIG. 2, a reduced-pressure system 200 is shown with another example of a wound. The wound in FIG. 2 is a subcutaneous wound 202 having an incisional opening in the epidermis 104 extending through the dermis 106 into a cavity within the subcutaneous tissue 208. The reduced-pressure system 200 is otherwise substantially similar to the reduced-pressure system of FIG. 1 and, as such, utilizes the same reference numerals used in FIG. 1 for the same components.

Referring back to FIG. 1 with reference to FIG. 2 as well, the reduced-pressure system 100 comprises a dressing assembly 110 positioned over the surface wound 102 and a reduced-pressure source 112 for providing a reduced pressure to the dressing assembly 110. The system 100 further comprises a canister 114 having a filter (not shown) contained within the canister 114 that is coupled in fluid communication with the reduced-pressure source 112 via a conduit 116. The canister 114 is also in fluid communication with the dressing assembly 110 via a second conduit 118 and a conduit connector 119. The canister 114 may be a fluid reservoir, or collection member, to filter or hold exudates and other fluids removed from the surface wound 102. In one embodiment, the canister 114 and the reduced-pressure source 112 are integrated into a single housing structure.

As used herein, the term "coupled" includes direct coupling or indirect coupling via separate object. The term "coupled" also encompasses two or more components that are continuous with one another by virtue of each of the components being formed from the same piece of material. Also, the term "coupled" may include chemical, mechanical, thermal, or electrical coupling. Fluid coupling means that fluid is in communication with the designated parts or locations.

The dressing assembly 110 further comprises a distribution manifold 120 adapted to be positioned at the opening of the surface wound 102, and a drape 122 adapted to cover the distribution manifold 120 to maintain reduced pressure beneath the drape 122 within the cavity of surface wound 102. The drape 122 includes an aperture 124 through which the conduit connector 119 extends to provide fluid communication between the second conduit 118 and the distribution manifold 120. The drape 122 also includes a periphery portion 126 that extends beyond the perimeter of the opening of the surface wound 102 that includes an adhesive or bonding agent (not shown) to secure the drape 122 to the healthy tissue adjacent the opening of the surface wound 102. In one embodiment, the adhesive disposed on the drape 122 may be used to provide a seal between the epidermis 104 and the drape 122 to maintain reduced pressure within the surface wound 102. In another embodiment, a seal layer (not shown) such as, for example, a hydrogel or other material, may be disposed between the drape 122 and the epidermis 104 to augment or substitute for the sealing properties of the adhesive.

The drape 122 may be any material that provides a pneumatic or fluid seal. The drape 122 may, for example, be an impermeable or semi-permeable, elastomeric material. "Elastomeric" means having the properties of an elastomer, and generally refers to a polymeric material that has rubber-like properties. More specifically, most elastomers have elongation rates greater than 100% and a significant amount of resilience. The resilience of a material refers to the material's ability to recover from an elastic deformation. Examples of elastomers may include, but are not limited to, natural rubbers, polyisoprene, styrene butadiene rubber, chloroprene rubber, polybutadiene, nitrile rubber, butyl rubber, ethylene propylene rubber, ethylene propylene diene monomer, chlorosulfonated polyethylene, polysulfide rubber, polyurethane, EVA film, co-polyester, and silicones. Specific examples of drape materials include a silicone drape, 3M Tegaderm® drape, V.A.C.™ Drape™, acrylic drape such as one available from Avery Dennison, or an incise drape.

The dressing assembly 110 further comprises a composite scaffold 130 positioned within the cavity of surface wound 102 in fluid communication with the manifold 120 for applying reduced pressure to the cavity of the surface wound 102 and to provide a structure for promoting the growth of tissue within the cavity of the surface wound 102. The composite scaffold 130 may be partially or fully in contact with the cavity walls of the surface wound 102 being treated. When the composite scaffold 130 is in contact with the walls of the surface wound 102, the composite scaffold 130 may partially or fully fill the void of the surface wound 102. The composite scaffold 130 may be any size, shape, or thickness depending on a variety of factors, such as the type of treatment being implemented or the nature and size of the cavity of the surface wound 102.

In one illustrative embodiment, the distribution manifold 120 is a foam material that distributes reduced pressure to the composite scaffold 130 and the cavity of the surface wound 102 when the distribution manifold 120 is in contact with or near the composite scaffold 130. The foam material may be either hydrophobic or hydrophilic. In one non-limiting example, the distribution manifold 120 is an open-cell, reticulated polyurethane foam such as GranuFoam® dressing available from Kinetic Concepts, Inc. of San Antonio, Tex. In the example in which the distribution manifold 120 is made from a hydrophilic material, the distribution manifold 120 also functions to wick fluid away from the composite scaffold 130 and the cavity of the surface wound 102, while continuing to provide reduced pressure to the composite scaffold 130 as a manifold. The wicking properties of the distribution manifold 120 draw fluid away from the cavity of the surface wound 102 by capillary flow or other wicking mechanisms. An example of a hydrophilic foam is a polyvinyl alcohol, open-cell foam such as V.A.C. WhiteFoam® dressing available from Kinetic Concepts, Inc. of San Antonio, Tex. Other hydrophilic foams may include those made from polyether. Other foams that may exhibit hydrophilic characteristics include hydrophobic foams that have been treated or coated to provide hydrophilicity.

Referring to FIG. 2, the reduced-pressure system 200 further comprises a flange portion 219 of the conduit connector 119 positioned between the drape 122 and the epidermis 104 and a third conduit 218 supported by the flange portion 219 and extending therefrom into the cavity of the subcutaneous wound 202. The reduced-pressure system 200 further comprises a distribution manifold 220 fluidly coupled to the conduit connector 119 via the third conduit 218. The distribution manifold 220 is substantially similar to the distribution manifold 120 (FIG. 1), but is constructed from bioresorbable materials that do not have to be removed from a patient's body following use of the dressing assembly 210. Suitable bioresorbable materials may include, without limitation, a polymeric blend of polylactic acid (PLA) and polyglycolic acid (PGA). The polymeric blend may also include, without limitation, polycarbonates, polyfumarates, and capralactones. The distribution manifold 220 may further serve as a scaffold for new cell-growth, or a scaffold material may be used in conjunction with the distribution manifold 220 to promote cell-growth. A scaffold is a substance or structure used to enhance or promote the growth of cells or formation of tissue, such as a three-dimensional porous structure that provides a template for cell growth. Illustrative examples of scaffold materials include calcium phosphate, collagen, PLA/PGA, coral hydroxy apatites, carbonates, or processed allograft materials.

Figure 3:
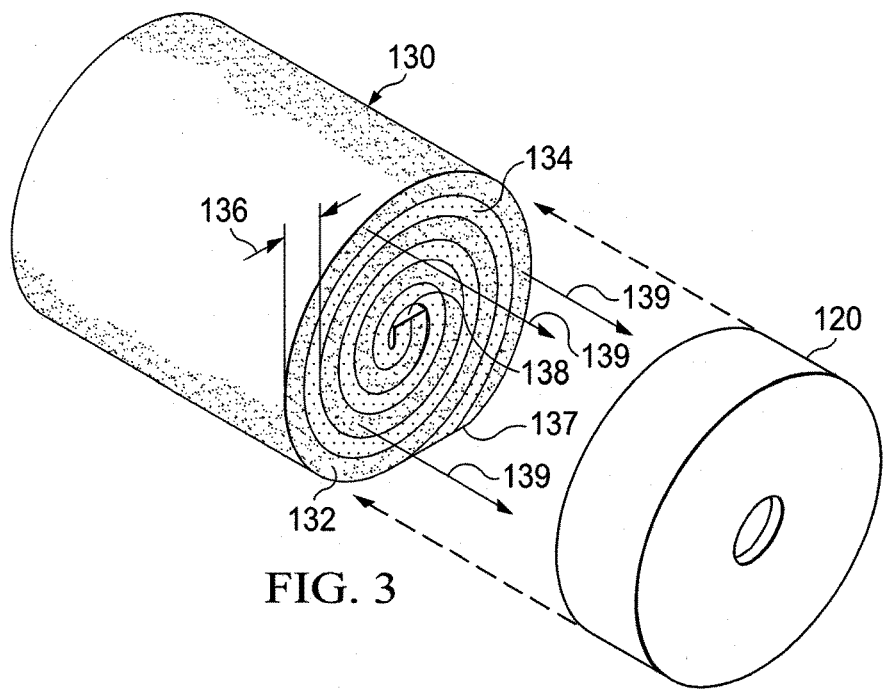
FIG. 3 is a schematic, perspective view, of the composite scaffold and the side-mounted manifold of FIGS. 1 and 2.

Referring to FIG. 3, the composite scaffold 130 comprises a strip of tissue such as, for example, adipose tissue sandwiched together with a strip of scaffold material, i.e., a tissue lamina 134 and a scaffold lamina 132, respectively, forming a laminate 136. The laminate 136 may then be rolled into a generally cylindrical shape as shown with one end portion rolled inside the composite scaffold 130, i.e., the internal end portion 138, and the other end portion rolled outside the composite scaffold 130, i.e., the external end portion 137. The surfaces of the scaffold lamina 132 are in fluid communication with the surfaces of the tissue lamina 134. In one embodiment, the scaffold lamina 132 is relatively thin and best suited for maintaining the viability of the tissue lamina 134 before and after being transferred to the cavities of the wounds 102, 202. In another embodiment, the scaffold lamina 132 is relatively thicker so that it not only maintains the viability of the tissue lamina 134, but also expands the tissue lamina 134 as the tissue lamina 134 grows into the scaffold lamina 132 increasing in volume and bulk while in the cavities of the wounds 102, 202. It should be understood that the composite scaffold 130 or laminate 136 may be treated in vitro with fluids or the application reduced pressure prior to being transferred to the patient and/or in vivo with native fluids from the cavities of the wounds 102, 202 or with other fluids as described below in conjunction with the system shown in FIG. 7.

When the composite scaffold 130 is positioned in the cavity of the surface wound 102 as described above, the manifold 120 is in fluid communication with the edges of the scaffold lamina 132 as described above and shown by arrows 139 in FIGS. 1A and 3. The scaffold lamina 132 is preferably bioabsorbable and as such will be absorbed as the tissue in the cavity of the surface wound 102 and the tissue lamina 134 grows in vivo to fill the cavity. As indicated above, the composite scaffold 130 may be rolled into any size and shape to fill or partially the fill the cavity of the surface wound 102 and the subcutaneous wound 202.

The tissue lamina 134 according to the invention may be any type of tissue desired for implantation, such as adipose tissue. In certain embodiments, the tissue of the tissue lamina 134 is the same type of tissue that surrounds a defect (e.g., wound) site. The tissue lamina 134 may be allograft, autograft, xenograft tissue or may be a tissue generated in vitro from a population of pluripotent cells. In certain aspects, the tissue lamina 134 comprises a substantially intact slice of tissue that is shaped to fit a scaffold lamina 132. In certain other aspects, the tissue lamina 134 may be composed of raw lipoaspirate or cells separated from the lipoaspirate.

The fluid communication between the scaffold lamina 132 and the tissue lamina 134 composed of adipose tissue allows the cells in the adipose tissue to remain viable while the introduced tissue undergoes neovascularization (or revascularization in the case of graft tissue). In particular, fluid flow through the tissue removes metabolic waste products from the tissue and draws nutrients such as oxygen from the surrounding tissue into the introduced tissue. Thus, fluid flow not only maintains the viability of cells in the tissue lamina 134, but also promotes proliferation of the cells and bulking a tissue defect such as the surface wound 102.

Figure 4:
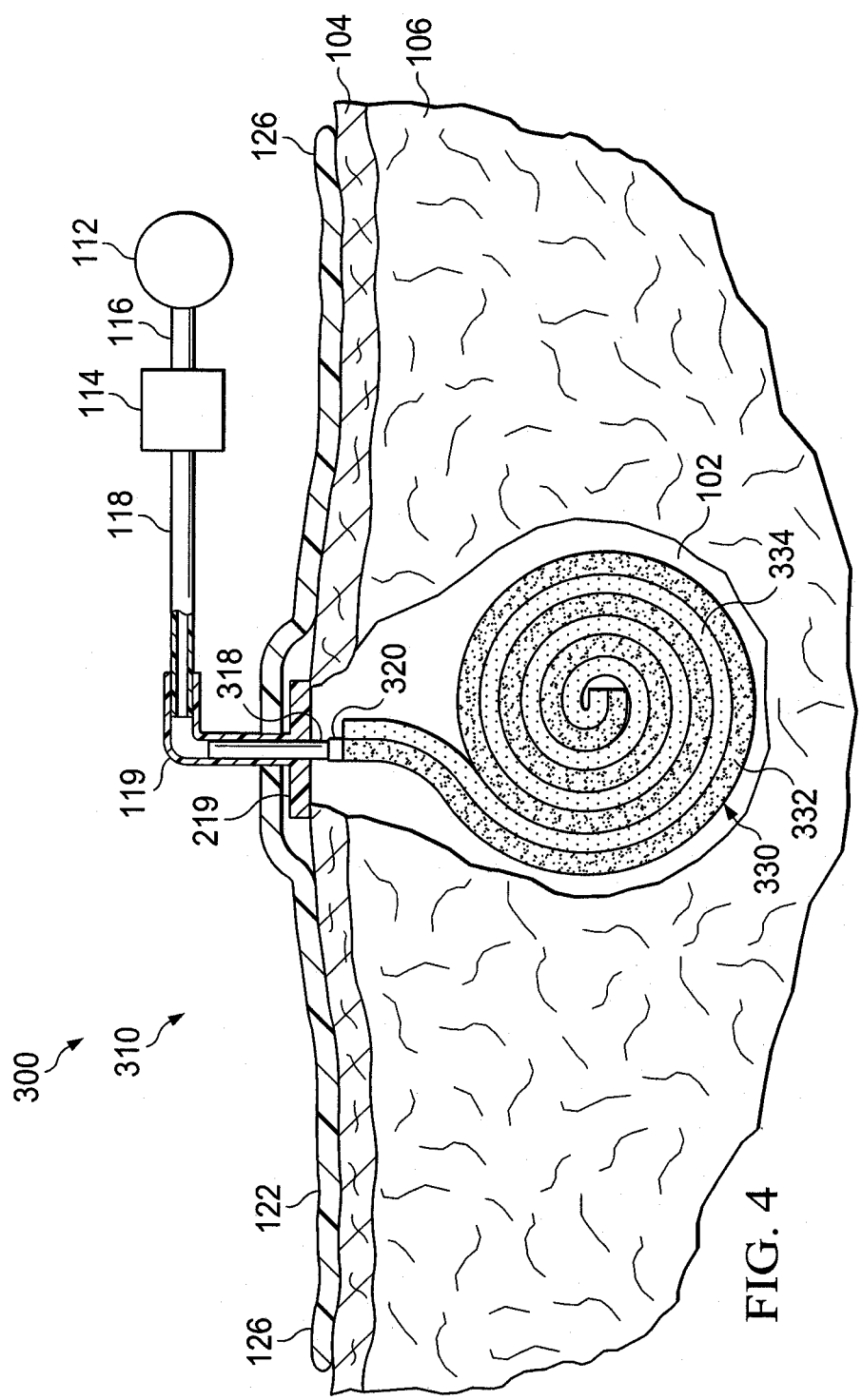
FIG. 4 is a schematic cross-section of a third illustrative embodiment of a system for treating a surface wound on a patient including a composite scaffold and an end-mounted manifold.
Figure 5:
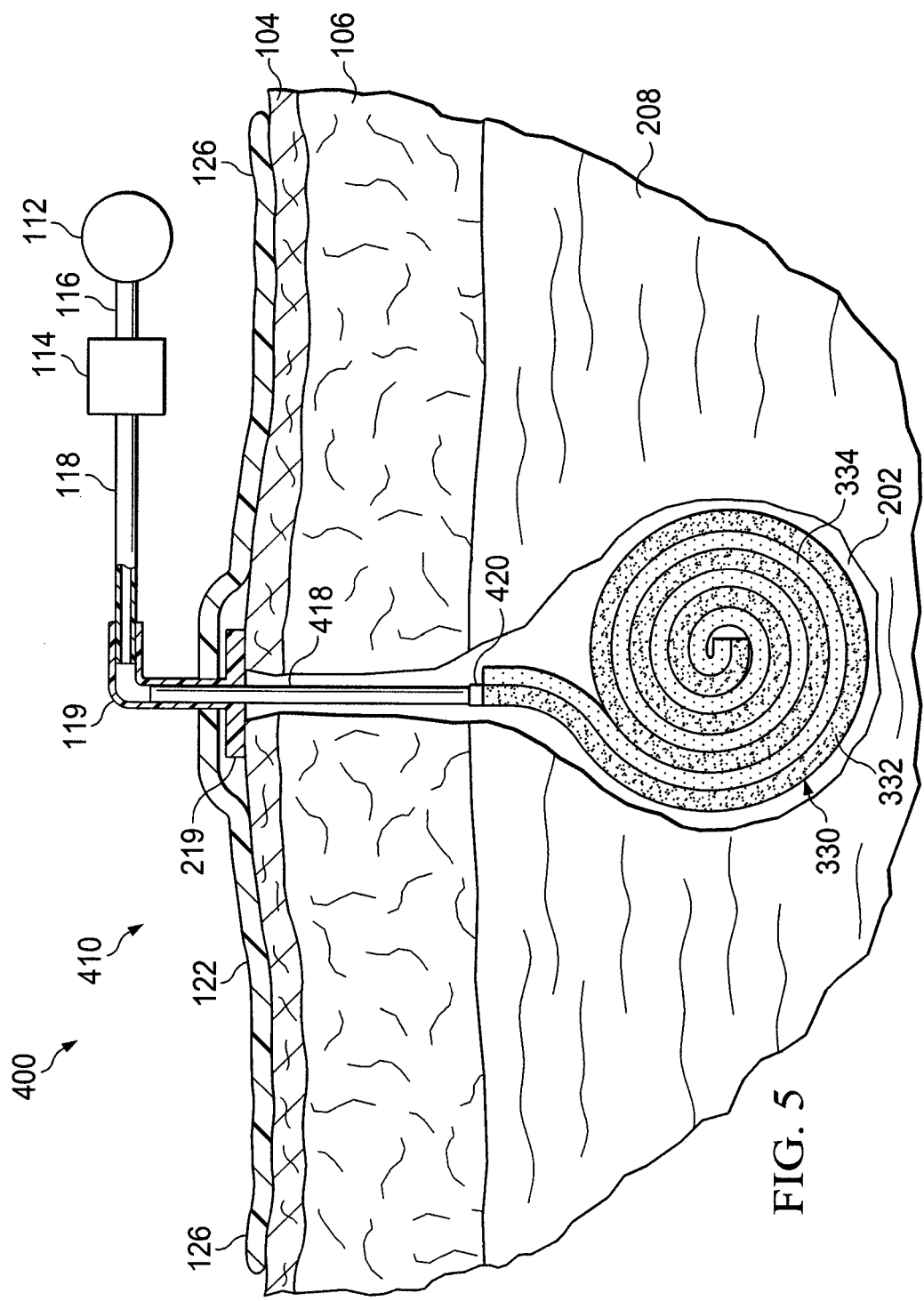
FIG. 5 is a schematic cross-section of a fourth illustrative embodiment of a system for treating a subcutaneous would on a patient including a composite scaffold and an end-mounted manifold.

Referring to FIG. 4, a third illustrative embodiment of a reduced-pressure system 300 for applying reduced pressure at a tissue site in the body of a patient to repair the surface wound 102 is shown and comprises the same components as the reduced-pressure system 100 in FIG. 1 as indicated by the reference numbers. Referring to FIG. 5, a fourth reduced-pressure system 400 for applying reduced pressure to the subcutaneous wound 202 is shown and comprises the same components as the reduced-pressure system 200 in FIG. 2 as indicated by the reference numbers. The reduced-pressure systems 300 and 400 are substantially the same as the systems 100 and 200, respectively, other than the manifolds and composite scaffolds. The reduced-pressure systems 300, 400 comprise a dressing assembly 310 and 410, respectively, each one of which includes a distribution manifold 320 and a composite scaffold 330.

Figure 6:
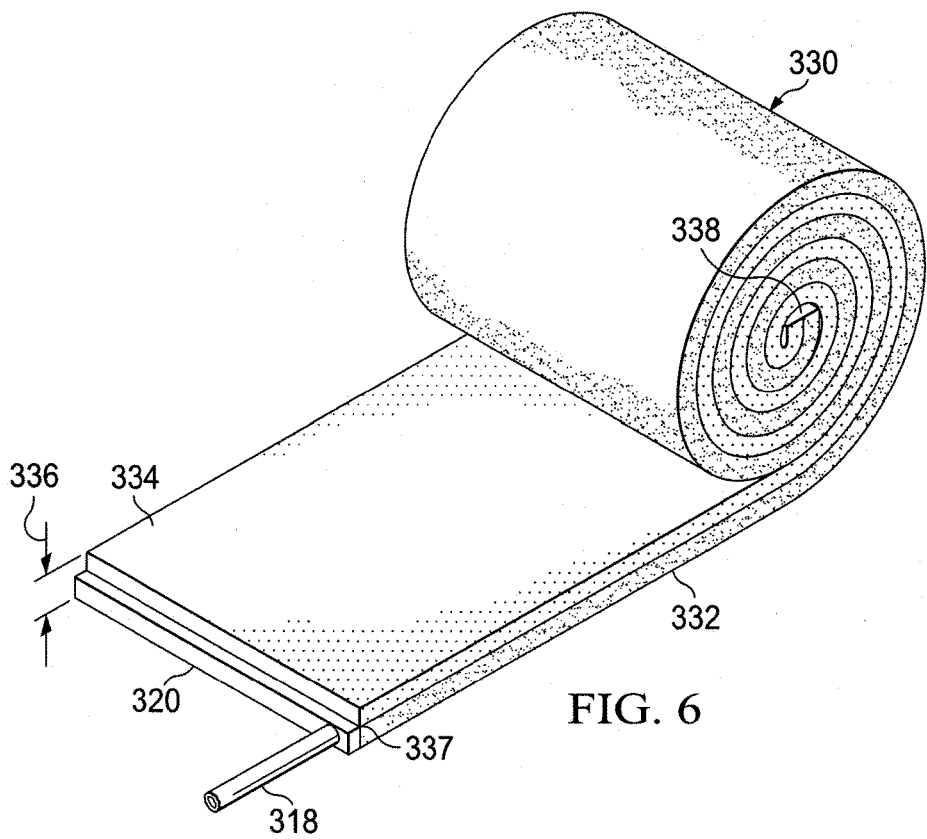
FIG. 6 is a schematic, perspective view, of the composite scaffold and the end-mounted manifold of FIGS. 4 and 5.

The composite scaffold 330 also comprises a scaffold lamina 332 and a tissue lamina 334 that form a laminate 336 which also may be rolled into a generally cylindrical shape as shown in FIG. 6. The rolled laminate 336 also has an external end portion 337 and an internal end portion 338 within the composite scaffold 330. In this embodiment, however, the distribution manifold 320 is fluidly coupled to the scaffold lamina 332 at the external end portion 337 of the composite scaffold 330 rather than at the edges of the scaffold lamina 332. The scaffold lamina 332 has sufficient porosity to fluidly communicate the reduced pressure to substantially the full length of the tissue lamina 334. The scaffold lamina 332 may have a porosity that increases toward the inside of the composite scaffold 330 to create a reduced-pressure gradient within the composite scaffold 330. Otherwise, the scaffold lamina 332 is substantially similar to the scaffold lamina 132. When the composite scaffold 330 is positioned in either type of wound 102, 202, the distribution manifold 320 is fluidly coupled to the third conduit 318 for distributing reduced pressure to the composite scaffold 330 as described above. In this embodiment, however, the composite scaffold 330 is oriented within the cavities of the wounds 102, 202 such that the longitudinal axis of the composite scaffold 330 is aligned generally parallel with the epidermis 104 rather than perpendicular. The structure and orientation of this distribution manifold 320 and composite scaffold 330 may be better suited for different types of wounds such as, for example, a surface or subcutaneous wound with an incisional cut through the epidermis 104 and the dermis 106.

Figure 7:
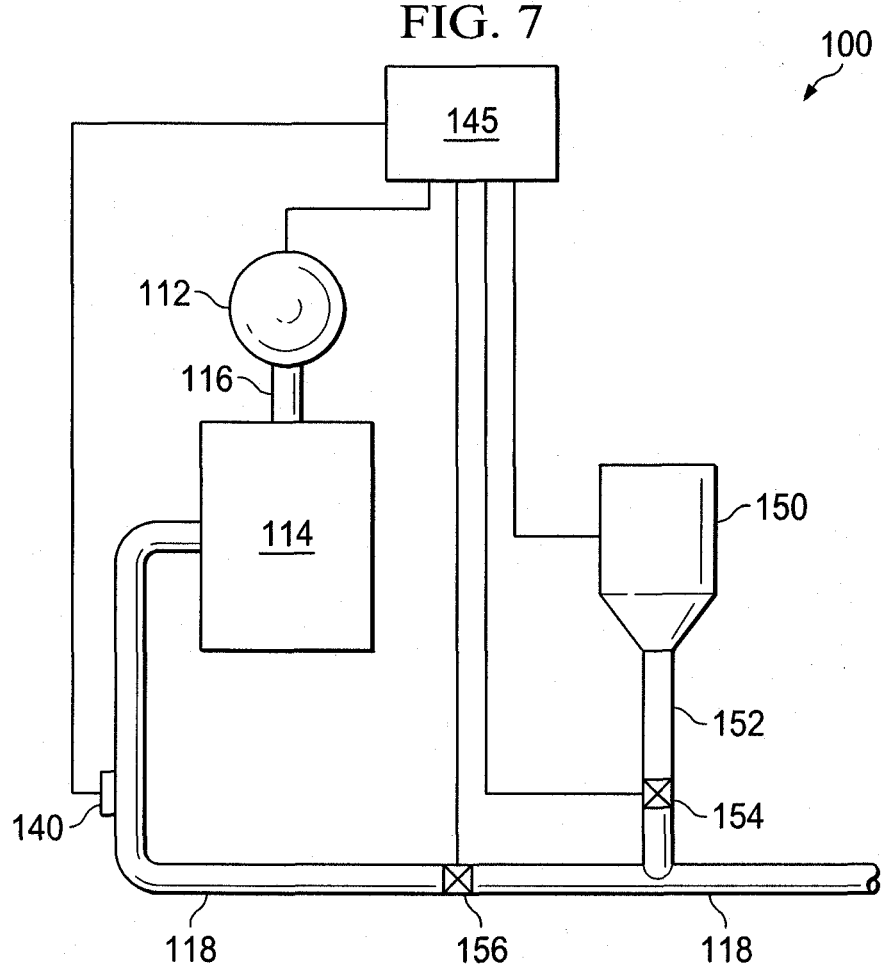
FIG. 7 is a schematic view of a fluid control system for the system shown in FIGS. 1A and 4.

Referring to FIG. 7, the reduced pressure therapy systems 100, 200, 300, and 400 (collectively, the "systems") may further comprise a pressure sensor 140 operably connected to the second conduit 118 to measure the reduced pressure being applied to the manifolds 120, 220, 320, and 420 (collectively, the "manifolds"). The systems further include a control unit 145 electrically connected to the pressure sensor 140 and the reduced pressure source 112. The pressure sensor 140 measures the reduced pressure within the cavity of the wounds 102, 202 (collectively, the "wounds") and also may indicate whether the second conduit 118 is occluded with blood or other bodily fluids. The pressure sensor 140 also provides feedback to control unit 145 which regulates the reduced pressure therapy being applied by the reduced pressure source 112 through the second conduit 118 to the manifolds. The reduced pressure therapy systems may also comprise a fluid supply 150 fluidly coupled to the second conduit 118 via a fourth conduit 152 and operatively connected to the control unit 145. The fluid source 150 may be used to deliver growth and/or healing agents to the scaffolds 130 and 330 (collectively, the "scaffolds") for the wounds including, without limitation, an antibacterial agent, an antiviral agent, a cell-growth promotion agent, an irrigation fluid, or other chemically active agents. The systems further comprise a first valve 154 positioned in the fourth conduit 152 to control the flow of fluid therethrough, and a second valve 156 positioned in the second conduit 118 between the reduced pressure supply 112 and the juncture between the second conduit 118 and the fourth conduit 152 to control the flow of reduced pressure. The control unit 145 is operatively connected to the first and second valves 154, 156 to control the delivery of reduced pressure and/or fluid from the fluid supply 150, respectively, to the manifolds as required by the particular therapy being administered to the patient. The fluid supply 150 may deliver the liquids as indicated above, but may also deliver air to the manifolds to promote healing and facilitate drainage at the site of the wounds.

In the embodiment illustrated in FIG. 7, the reduced-pressure source 112 is an electrically-driven vacuum pump. In another implementation, the reduced-pressure source 112 may instead be a manually-actuated or manually-charged pump that does not require electrical power. The reduced-pressure source 112 instead may be any other type of reduced pressure pump, or alternatively a wall suction port such as those available in hospitals and other medical facilities. The reduced-pressure source 112 may be housed within or used in conjunction with a reduced pressure treatment unit (not shown), which may also contain sensors, processing units, alarm indicators, memory, databases, software, display unites, and user interfaces that further facilitate the application of reduced pressure treatment to the wounds. In one example, a sensor or switch (not shown) may be disposed at or near the reduced-pressure source 112 to determine a source pressure generated by the reduced-pressure source 112. The sensor may communicate with the control unit 145 that monitors and controls the reduced pressure that is delivered by the reduced-pressure source 112.

As used herein, the term "manifold" refers to a substance or structure that is provided to assist in directing reduced pressure to, delivering fluids to, or removing fluids from a tissue site. A manifold can include a plurality of flow channels or pathways that are interconnected to improve distribution of fluids provided to and removed from the area of tissue around the manifold. Examples of manifolds may include, without limitation, devices that have structural elements arranged to form flow channels, cellular foams such as open-cell foam, porous tissue collections, and liquids, gels and foams that include or cure to include flow channels. A detailed description of manifolds and their use according to the invention is provided below.

The term "scaffold" as used herein refers to a substance or structure applied to or in a wound or defect that provides a structural matrix for the growth of cells and/or the formation of tissue. A scaffold is often a three dimensional porous structure. The scaffold can be infused with, coated with, or comprised of cells, growth factors, extracellular matrix components, nutrients, integrins, or other substances to promote cell growth. A scaffold can take on characteristics of a manifold by directing flow through the matrix. A manifold can transmit flow to the scaffold and tissue; in the context of reduced pressure treatment, the manifold can be in fluid communication with the scaffold. A detailed description of scaffolds and their use according to the invention is provided below.

As such, the invention disclosed here discloses methods and apparatuses for controlling cellular-level based patterns of fluid flow that would allow for control of patterned protein organization at a microscopic, nanoscopic, or mesoscopic scale amenable to provide a structured manifold and, optionally, a scaffold material for cellular migration, differentiation, and like behavior necessary for functional regeneration of tissues. In comparison to the passive nature of the current state of the art with regards to tissue repair and regeneration, the methods, scaffolds, manifolds, flow sources and systems disclosed herein provide an active mechanism by which to promote the endogenous deposition of proteins and organization of the provisional matrix with biochemical and physical cues to direct cellular colonization of a scaffold or tissue space. The present invention thus enhances current technology by exploiting the active force of directed fluid flow, providing a framework upon which to design manifolds and scaffolds based upon the need of the biology under the influence of fluid flow. Flow vectors and pathways are utilized to enhance protein deposition and cellular colonization. The systems provided herein are designed to promote establishment of a provisional matrix network with a seamless transition from the healthy tissue edges through a scaffold or tissue site to promote a functional tissue continuum.

Thus, the apparatuses, methods and systems disclosed herein provide a means for active guidance of tissue regeneration through an implanted scaffold or within a tissue site to promote functional recovery. This active guidance occurs through mechanisms of controlled fluid flow, which can be used to initiate or augment the early stages of the body's own natural healing process; a manifold can provide the active guidance necessary to create a controlled fluid flow. Specifically, the controlled flow vectors that the manifolds provide can be used to facilitate the directed influx of cells and proteins into a scaffold. Creation of specific flow pathways within a tissue site or scaffold can lead to patterned deposition of proteins, such as collagen and fibrin within the manifold, scaffold or tissue space. Biochemical cues from cytokines, growth factors, and cells bound within the provisional matrix can work in conjunction with the natural physical cues of the provisional matrix and extracellular matrix to guide the subsequent migration of endogenous cells during the repair stages of healing. These cues act as a form of track that emanates from the healthy tissues and passes through the scaffolding or tissue space to facilitate a continuous guidance pathway for organized tissue regeneration.

To that end, this disclosure provides unique manifolding technologies designed for specific biological needs based upon principles of fluid flow. In certain aspects, the invention concerns a new approach to wound healing, flow (or gradient) activated tissue engineering. In rudimentary form, this approach involves a source or generator of flow that forms a gradient for controlled movement of either endogenous or exogenous fluids into, out of, or through a tissue space for the organized deposition of proteins and/or spatial concentration of cytokines and growth factors, with subsequent formation of a directionally oriented provisional matrix. The tissue space being defined here includes, but is not limited to, the region surrounding a site of tissue deficit or damage, including a wound or incision.

Fluid flow into, through, or out of the tissue space can be refined and directed through the inclusion of additional elements to the system including manifolds and/or scaffolds. The coordinated elements of the system are designed to create flow parameters, pathways, and patterns sufficiently detailed in scale as to be able to influence and direct the controlled adsorption of proteins, the organization of matrix, and organized colonization of specific cell types. Individual elements of the system are as follows.

Source or Generator of Flow.

Flow is induced into, through, or out of the tissue space by methods or apparatuses that introduce changes in mechanical, chemical, and/or electrical potentials. These generators of flow provide either a gradient or a change in potential from the site or reservoir of endogenous or exogenous fluids to the placement position of the flow generator or its extension element (i.e., manifold or scaffold). In one embodiment, the source of flow comprises a source of reduced pressure. Systems and apparatuses according to the invention may also comprise valves or arrays of valves that control the application and amount of negative pressure applied to the manifold. In certain aspects, scaffolds and/or manifolds described herein comprise a pressure sensor. Thus, in some embodiments, the amount of negative pressure applied by a source is regulated based on the amount of negative pressure that is sensed in the manifold or scaffold or at the site of tissue damage.

Manifold.

The flow generators are the driving force for stimulating the flow of fluids. Manifolds are apparatuses for refining the pattern of flow between the source or generator of flow and the tissue space. The macroscale level of flow is refined by specialized manifolds utilized for directed localization to a single point or to a plurality of selectively positioned points for creating initiation sites for microscale flow pathways within the manifold/scaffold and, ultimately, the tissue space. The manifold may also serve as a conduit for the removal of fluids from and as an apparatus for the delivery of exogenous fluids to the tissue space.

A manifold generally refers to a physical substance or structure that serves to assist in applying and translating a mechanical, chemical, electrical or similar alterations into changes in the flow of a fluid, herein defined as the movement of liquids, gases, and other deformable substances such as proteins, cells, and other like moieties. As such, this physical device includes a single point or plurality of points for the egress or evacuation of pressure, fluids, and like substances capable of translating the movement of fluids in a scaffold, as defined above. This can include, but is not limited to, the introduction of exogenous factors such as cells and/or therapeutic moieties into the scaffold through the lumen or plurality of lumens present in the manifold. In addition, as used herein, a manifold includes a single point or plurality of points for the ingress or introduction of fluid from the scaffold back towards the point source of flow.

Flow distributed by the manifold can direct the movement of endogenous proteins, growth factors, cytokines, and cells from their resident locations within the host to the tissue space or scaffold in an organized manner. The establishment of flow along these pathways leads to the deposition of proteins and provisional matrix that creates an interfacial endogenous network connecting the host to the scaffold. Extensions of this matrix can be established within the scaffold through selective positioning of the manifold flow initiation sites with flow promoting scaffolding designs. The organized protein deposition and provisional matrix provide a biochemical and physical framework that stimulates the attachment and migration of cells along directed pathways throughout the scaffold and the tissue space. The resulting endogenous network of proteins, growth factors, and cells provides a foundation upon which subsequent phases of the body's own tissue repair and regeneration mechanisms can build.

When in place, the manifold works in conjunction with a flow generating source and a scaffold, if present. Flow generating sources include, but are not limited to generators of negative pressure; generators of positive pressure; and generators of osmotic flow. The flow gradient established in the manifold may be further refined through the scaffold, to deliver a flow gradient to the scaffold to optimize flow through the scaffold as needed for the particular defect. Many of the embodiments disclosed herein are manifolds capable of translating changes in pressure and the like into controlled movement of fluids, optionally through a physical scaffold, for the purposes of directed tissue regeneration. These embodiments are generally specified for a particular application in the regeneration of specific tissues, but are not limited to a particular tissue therein.

In order to realize the goal of inducing flow for the purpose of tissue regeneration, alterations in the aforementioned mechanical, chemical, or electrical impetus must be translated from the singular gradient source toward a physical substrate or scaffold to elicit cellular-level changes in protein adsorption, matrix organization, cell migration, and other tissue regeneration-related behaviors. These alterations are multivariate in nature and can include mechanical changes that elicit a physical change in pressure applied to the scaffold as applied to the site of the wound or desired site of tissue regeneration, chemical changes that elicit a gradient in protein and/or ion concentrations, which result in the creation of osmotic gradients capable of inducing flow, or electrical changes that create a gradient of current/ion exchange allowing for propagation of electrical signals from the point source. It is to be understood, however, that the applicants are not bound by any particular mechanism through which gradients and fluid flow induce advantageous results in tissue repair or growth. In order to advantageously transmit these gradients to the tissue, a physical device is needed to direct the path of flow from its source to the scaffold or tissue site and vice versa.

In some embodiments, the manifold comprises a physical structure in close apposition to or within the contents of a scaffold and serves to propagate an alteration in a physical parameter, whether it be mechanical, chemical, electrical, or something similar in nature, for the means of directing these changes from its point source to the scaffolding material. The placement of this manifold with respect to its location with regard to that of the scaffold may be of crucial importance for facilitating controlled and directed regeneration of specific tissue types. For example, the manifold may be situated such that implanted tissue, such as a tissue lamina, is between the manifold and blood source at a tissue site so that fluid from the blood source or interstitial fluids can flow to or through the implanted tissue Manifolds may be composed of a bioabsorbable or bioinert material. Examples include non-bioabsorbable materials such as medical grade silicone polymers, metals, polyvinylchloride (PVC), and polyurethane (e.g., GranuFoam®). Bioabsorbable polymers such as collagen, polylactic acid (PLA), polyglycolic acid (PGA), polylactide-co-glycolide (PLGA), a polysaccharide (e.g., alginates), a hydrogel, or a polyethylene glycol, or combinations thereof, can also be used. In certain aspects, a manifold is composed of a mechanically stiff materials such as a calcium phosphate, hydroxyapatite, DBM, carbonates or bioglass. Such mechanically stiff materials may have particular use in filling hard tissue defects. Some manifolds are also a mix of non-bioresorbable and bioresorbable materials. In general material used for a scaffold may also be used to compose a manifold and such materials are further detailed below. In certain aspects, manifold materials are structured to include a high void fraction for improved bioabsorption properties. In some embodiments, the manifold may embody characteristics of the scaffold.

Scaffold.

Biologic and synthetic scaffolds are used in the field of tissue engineering to support protein adhesion and cellular ingrowth for tissue repair and regeneration. The current state of the art in scaffold technology relies upon the inherent characteristics of the surrounding tissue space for the adsorption of proteins and migration of cells. A scaffold for use according to the invention is coupled to a manifold, provides physical guidance to direct the pathway of fluid flow in the tissue site, creating avenues for the movement and migration of adhesive proteins and cells, respectively, which are integral to the establishment of a provisional matrix in predetermined patterns of organization within the tissue space. The methods and apparatuses described for fluid flow-induced and gradient-induced generation of tissues have direct implications into the design of the scaffolds. Within this context, scaffolds serve to refine the pathways of fluid flow within the tissue space to cellular level patterns from the fluid source to the point(s) of flow initiation within the manifold. A scaffold may embody characteristics of a manifold or be combined in conjunction with a manifold for refinement of the flow pathways within the tissue site. In certain aspects, a scaffold is a reticulated structure comprising high void fraction for improved bioabsorption properties.

Nonlimiting examples of suitable scaffold materials include extracellular matrix proteins such as fibrin, collagen or fibronectin, and synthetic or naturally occurring polymers, including bioabsorbable or non-bioabsorbable polymers, such as polylactic acid (PLA), polyglycolic acid (PGA), polylactide-co-glycolide (PLGA), polyvinylpyrrolidone, polycaprolactone, polycarbonates, polyfumarates, caprolactones, polyamides, polysaccharides (including alginates (e.g., calcium alginate) and chitosan), hyaluronic acid, polyhydroxybutyrate, polyhydroxyvalerate, polydioxanone, polyethylene glycols, poloxamers, polyphosphazenes, polyanhydrides, polyamino acids, polyortho esters, polyacetals, polycyanoacrylates, polyurethanes, polyacrylates, ethylene-vinyl acetate polymers and other acyl substituted cellulose acetates and derivatives thereof, polystyrenes, polyvinyl chloride, polyvinyl fluoride, poly(vinylimidazole), chlorosulphonated polyolefins, polyethylene oxide, polyvinyl alcohol, Teflon®, and nylon. The scaffold can also comprise ceramics such as hydroxyapatite, coralline apatite, calcium phosphate, calcium sulfate, calcium carbonate or other carbonates, bioglass, allografts, autografts, xenografts, decellularized tissues, or composites of any of the above. In particular embodiments, the scaffold comprises collagen, polylactic acid (PLA), polyglycolic acid (PGA), polylactide-co-glycolide (PLGA), a polyurethane, a polysaccharide, an hydroxyapatite, or a polytherylene glycol. Additionally, the scaffold can comprise combinations of any two, three or more materials, either in separate areas of the scaffold, or combined noncovalently, or covalently (e.g., copolymers such as a polyethylene oxide-polypropylene glycol block copolymers, or terpolymers), or combinations thereof. Suitable matrix materials are discussed in, for example, Ma and Elisseeff, 2005, and Saltzman, 2004.

Bioactive Agents

In certain aspects, the apparatuses and methods according to the invention concern bioactive agents. Bioactive agents may, in some cases, be incorporated directly onto a manifold or scaffold material (i.e., to generate a bioactive manifold and/or scaffold). For example, agents that facilitate tissue growth such as collagen or fibrin may be directly incorporated onto or into a manifold or scaffold material. Likewise, in applications where aberrant immune response need be avoided (e.g., tissue grafts) immune regulator agents such as rapamycin may be incorporated into manifold or scaffold structures.

In further aspects soluble bioactive agents may be introduced at a site of tissue damage by virtue of the flow through the tissue site. For example, a manifold may be in fluid communication with a fluid source and a bioactive agent may be introduced into the fluid source and thereby into the manifold and tissue lamina.

Nonlimiting examples of useful bioactive growth factors for various applications are growth hormone (GH), a bone morphogenetic protein (BMP), transforming growth factor-α (TGF-α), a TGF-β, a fibroblast growth factor (FGF), granulocyte-colony stimulating factor (G-CSF), granulocyte/macrophage-colony stimulating factor (GM-CSF), epidermal growth factor (EGF), platelet derived growth factor (PDGF), insulin-like growth factor (IGF), vascular endothelial growth factor (VEGF), hepatocyte growth factor/scatter factor (HGF/SF), an interleukin, tumor necrosis factor-α (TNF-α) or nerve growth factor (NGF). In certain applications, the bioactive molecule may be a molecule that directs vascularization such as VEGF.

Tissue Repair and Regeneration.

The apparatuses and systems disclosed herein can be used for tissue repair and engineering in various contexts including the following.

Repair and Regeneration of Lost Tissue.

A generator of flow may be combined with manifolds and/or scaffolds to direct the regeneration of lost tissue at a site of injury or compromised function. Tissues lost from traumatic injury, surgery, burns, or other causes (e.g., infection or autoimmune disease) can be led to regenerate using the methods, scaffolds, manifolds, flow sources and systems of the invention.

Retard the Progression of a Tissue Disease State.

A generator of flow may be combined with manifolds and/or scaffolds to retard disease progression of an affected tissue such as occurs, e.g., in autoimmune disease and wasting infections such as a Staph infection.

Maintenance of Tissue Viability.

A generator of flow may be combined with manifolds and/or scaffolds to maintain the viability of explanted tissues, such as adipose tissues, either for in vitro study, ex vivo scaffold or implant preparation, or in vivo transplant. A generator of flow combined with a manifold may be used to provide nutrient fluid flow to the tissue and to control waste removal from the tissue.

Expansion of Tissue.

A generator of flow may be combined with manifolds and/or scaffolds to promote the expansion of existing tissues. The methods, scaffolds, manifolds, flow sources and systems of the invention can be used to direct the growth of tissues where additional tissue quantity is needed or desired. Tissue expansion may be accomplished either in vivo or ex vivo, for example in a tissue culture environment that provides required nutrients to the tissue wherein the nutrients are infused by the application of reduced pressure.

Acceleration of Tissue Formation or Promoting New Tissue Formation.

A generator of flow may be combined with manifolds and/or scaffolds to accelerate the rate of tissue formation within a natural healing response. The methods, scaffolds, manifolds, flow sources and systems of the invention may be used to accelerate tissue growth by augmenting formation of provisional matrices, facilitating its stable positioning, and aiding in recruitment of cells to the tissue space. Likewise, the apparatuses and methods disclosed herein may be used to promote new tissue formation at a selected tissue site. Such new tissue formation may be used to bulk (i.e., add volume and mass) a tissue site. Such methods may be used to rebuild tissue features that were lost to an injury, malformed during development or to improve the external appearance of a feature.

Stimulating the Differentiation of Stem Cells Along Specific Pathways.

A generator of flow may be combined with manifolds and/or scaffolds to stimulate the differentiation of stem cells or other pluripotent cells into specific lineages. Application of flow using the methods, scaffolds, manifolds, flow sources and systems of the invention may be used to direct pluripotent cells into specific cell lineages needed to foster growth in the tissue space. For example, adipose (e.g., brown or white adipocyte) progenitor cells may be provided as part of a tissue lamina and grown on a matrix either in vitro or at a tissue site in vivo.

Introducing Proteins, Matrix, Cells, or Pharmaceuticals into the In Vivo Environment.

A generator of flow may be combined with manifolds and/or scaffolds to introduce exogenous growth factors, proteins, cells, or pharmaceutical agents into the tissue space to augment tissue repair, regeneration, and/or maintenance.

Creating Matrices In Vitro for Implantation In Vivo.

A generator of flow may be combined with manifolds and/or scaffolds to facilitate formation of matrices in vitro that may subsequently be used for in vivo transplantation.

Promoting Integration of Transplanted Tissue.

A generator of flow may be combined with manifolds and/or scaffolds to promote integration of transplanted tissue into the host environment. This can be applied to autograft, allograft, or xenograft transplants. Transplanted tissues may be whole sections of tissue excised from surrounding tissue, or substantially disrupted tissues such as lipoaspirate. In such applications manifold material may include immune suppressing agents to reduce the chance of tissue rejection.

Directing Extracellular Matrix (ECM) Deposition and Orientation In Vitro.

A flow generator may be combined with manifolds and/or scaffolds to guide the directed deposition and orientation of ECM expressed by cells and tissues. The directed orientation of ECM has an impact in organizing and directing the attachment and colonization of subsequent cell layers and tissues.

All references cited in this specification are hereby incorporated by reference. The discussion of the references herein is intended merely to summarize the assertions made by the authors and no admission is made that any reference constitutes prior art. Applicants reserve the right to challenge the accuracy and pertinence of the cited references.

In view of the above, it will be seen that the advantages of the invention are achieved and other advantages attained. As various changes could be made in the above methods and compositions without departing from the scope of the invention, it is intended that all matter contained in the above description and shown in the accompanying drawings shall be interpreted as illustrative and not in a limiting sense.

We claim:

1. An apparatus for treating a wound having a cavity, the apparatus comprising:
a scaffold having a generally cylindrical shape, having a first end surface adapted to be inserted into the cavity of the wound and a second end surface adapted to receive reduced pressure from a pressure source to be provided to the wound, and comprising:
(i) a scaffold lamina being formed from a strip of material having surfaces extending between two edges, wherein the material includes a reticulated foam having a porous structure adapted to provide a structural matrix for the formation of tissue within the cavity of the wound and support protein adhesion, and
(ii) a tissue lamina being formed from a strip of material having surfaces extending between two edges, wherein the surfaces of the tissue lamina and the scaffold lamina are in fluid communication and rolled into the generally cylindrical shape of the scaffold, and wherein the edges of the tissue lamina and the scaffold lamina form the first and second end surfaces of the scaffold, respectively; and
a manifold adapted to be in fluid communication with the pressure source and the second end surface of the scaffold to provide reduced pressure to the scaffold lamina and the wound.

2. The apparatus of claim 1, further comprising a drape formed of substantially impermeable material to cover the scaffold and the manifold within the wound to substantially maintain the reduced pressure within the wound when provided by the manifold.

3. The apparatus of claim 1, wherein the manifold is positioned adjacent the second end surface of the scaffold.

4. The apparatus of claim 1, wherein the manifold is in fluid communication with an end portion of the scaffold lamina.

5. The apparatus of claim 1, wherein the tissue lamina comprises adipose tissue.

6. The apparatus of claim 5, wherein the adipose tissue is derived from lipoaspirate.

7. The apparatus of claim 1, wherein the tissue lamina comprises allograft, autograft or xenograft tissue.

8. The apparatus of claim 1, wherein the scaffold lamina is formed from a bioinert or bioabsorbable material.

9. The apparatus of claim 1, wherein the scaffold lamina is formed from a foam or gel material.

10. The apparatus of claim 1, wherein the scaffold lamina comprises a bioactive agent selected from the group consisting of an antibiotic, an antibody and a growth factor.

11. The apparatus of claim 10, wherein the bioactive agent is a growth hormone (GH), a bone morphogenetic protein (BMP), transforming growth factor-α (TGF-α), a TGF-β, a fibroblast growth factor (FGF), granulocyte-colony stimulating factor (G-CSF), granulocyte/macrophage-colony stimulating factor (GM-CSF), epidermal growth factor (EGF), platelet derived growth factor (PDGF), insulin-like growth factor (IGF), vascular endothelial growth factor (VEGF), hepatocyte growth factor/scatter factor (HGF/SF), an interleukin, tumor necrosis factor-α (TNF-α) or nerve growth factor (NGF).

12. The apparatus of claim 8, wherein the scaffold lamina comprises collagen.

13. The apparatus of claim 1, wherein the manifold comprises a bioinert material.

14. The apparatus of claim 1, wherein the manifold comprises a bioabsorbable material.

15. The apparatus of claim 1, wherein the scaffold lamina comprises a high void fraction for cell growth and tissue formation.

16. The apparatus of claim 1, wherein the scaffold lamina comprises a material configured to support cellular ingrowth.

17. The apparatus of claim 1, wherein a thickness of the scaffold lamina is greater than a thickness of the tissue lamina.

18. A method for treating a wound having a cavity, the method comprising:
positioning a scaffold within the cavity of the wound to provide reduced pressure to the wound, the scaffold having a generally cylindrical shape, having a first end surface adapted to be inserted into the cavity of the wound and a second end surface adapted to receive reduced pressure from a pressure source to be provided to the wound, and comprising:
(i) a scaffold lamina being formed from a strip of material having surfaces extending between two edges, wherein the material includes a reticulated foam having a porous structure adapted to provide a structural matrix for the formation of tissue within the cavity of the wound and support protein adhesion, and
(ii) a tissue lamina being formed from a strip of material having surfaces extending between two edges, wherein the surfaces of the tissue lamina and the scaffold lamina are in fluid communication and rolled into the generally cylindrical shape of the scaffold, and wherein the edges of the tissue lamina and the scaffold lamina form the first and second end surfaces of the scaffold, respectively; and
positioning a manifold in fluid communication with the second end surface of the scaffold to provide reduced pressure to the scaffold lamina and the wound, thereby treating the wound having a cavity.

19. The method of claim 18, further comprising the step of covering the scaffold and the manifold within the wound with a substantially impermeable material to substantially maintain the reduced pressure within the wound when provided by the manifold.

20. The method of claim 18, further comprising positioning the manifold adjacent the second end surface of the scaffold.

21. The method of claim 18, further comprising positioning the manifold in fluid communication with an end portion of the scaffold lamina.

22. The method of claim 18, wherein the tissue lamina comprises adipose tissue.

23. The method of claim 22, wherein the adipose tissue is derived from lipoaspirate.

24. The method of claim 18, wherein the tissue lamina comprises allograft, autograft or xenograft tissue.

25. A method for bulking a tissue site, the method comprising:

positioning a scaffold within the tissue site to provide reduced pressure to the tissue site, the scaffold having a generally cylindrical shape having a first end surface adapted to be inserted into the tissue site and a second end surface adapted to receive reduced pressure from a pressure source to be provided to the tissue site, and comprising:

(i) a scaffold lamina being formed from a strip of material having surfaces extending between two edges, wherein the material includes a reticulated foam having a porous structure adapted to provide a structural matrix for the formation of tissue within the tissue site and support protein adhesion, and (ii) a tissue lamina being formed from a strip of material having surfaces extending between two edges, wherein the surfaces of the tissue lamina and the scaffold lamina are in fluid communication and rolled into the generally cylindrical shape of the scaffold, and wherein the edges of the tissue lamina and the scaffold lamina form the first and second end surfaces of the scaffold, respectively; and positioning a manifold in fluid communication with the second end surface of the scaffold to provide reduced pressure to the scaffold lamina and the tissue site, thereby bulking the tissue site.

26. The method of claim 25, further comprising the step of covering the scaffold and the manifold within the wound with a substantially impermeable material to substantially maintain the reduced pressure within the tissue site when provided by the manifold.

27. The method of claim 25, further comprising positioning the manifold adjacent the second end surface of the scaffold.

28. The method of claim 25, further comprising positioning the manifold in fluid communication with an end portion of the scaffold lamina.

29. The method of claim 25, wherein the tissue lamina comprises adipose tissue.

30. The method of claim 29, wherein the adipose tissue is derived from lipoaspirate.

31. The method of claim 25, wherein the tissue lamina comprises allograft, autograft or xenograft tissue.

* * * * *